(12) United States Patent
Serizawa

(10) Patent No.: US 9,119,808 B1
(45) Date of Patent: Sep. 1, 2015

(54) TREATING NEURODEGENERATIVE DISEASES WITH GGA OR A DERIVATIVE THEREOF

(71) Applicant: COYOTE PHARMACEUTICALS, INC., Menlo Park, CA (US)

(72) Inventor: Hiroaki Serizawa, Menlo Park, CA (US)

(73) Assignee: Coyote Pharmaceuticals, Inc., Menlo Park, CA (US)

( * ) Notice: Subject to any disclaimer, the term of this patent is extended or adjusted under 35 U.S.C. 154(b) by 0 days.

(21) Appl. No.: 14/045,219

(22) Filed: Oct. 3, 2013

Related U.S. Application Data

(60) Provisional application No. 61/711,162, filed on Oct. 8, 2012.

(51) Int. Cl.
 *A61K 31/12* (2006.01)
 *A61K 31/121* (2006.01)

(52) U.S. Cl.
 CPC .................... *A61K 31/121* (2013.01)

(58) Field of Classification Search
 CPC ...................................... A61K 31/12
 USPC ......................................... 514/675
 See application file for complete search history.

(56) References Cited

U.S. PATENT DOCUMENTS

| | | | |
|---|---|---|---|
| 3,939,202 A | 2/1976 | Matsui et al. | |
| 4,059,641 A | 11/1977 | Mishima et al. | |
| 4,169,157 A | 9/1979 | Kijima et al. | |
| 4,281,019 A | 7/1981 | Shepherd | |
| 4,900,749 A | 2/1990 | Matsumoto et al. | |
| 4,977,170 A | 12/1990 | Matsumoto et al. | |
| 5,344,850 A | 9/1994 | Hata et al. | |
| 5,427,775 A | 6/1995 | Sakai et al. | |
| 5,453,524 A | 9/1995 | Tagami et al. | |
| 5,560,907 A | 10/1996 | Sakai et al. | |
| 5,574,025 A | 11/1996 | Anthony et al. | |
| 5,851,783 A | 12/1998 | Appel et al. | |
| 6,080,779 A | 6/2000 | Gasper et al. | |
| 6,090,407 A | 7/2000 | Knight et al. | |
| 6,130,048 A | 10/2000 | Nixon | |
| 6,391,553 B1 | 5/2002 | Chartier-Harlin et al. | |
| 6,699,850 B2 | 3/2004 | Reszka et al. | |
| 6,846,845 B2 | 1/2005 | Takahashi et al. | |
| 7,087,649 B2 * | 8/2006 | Barth et al. ................ | 514/675 |
| 7,268,124 B2 | 9/2007 | Wiemer et al. | |
| 7,341,988 B2 | 3/2008 | Nishizono et al. | |
| 7,356,521 B2 | 4/2008 | Wang et al. | |
| 7,563,244 B2 | 7/2009 | Kent et al. | |
| 7,678,078 B1 | 3/2010 | Peyman et al. | |
| 2002/0082244 A1 | 6/2002 | Reszka et al. | |
| 2003/0134907 A1 | 7/2003 | Takahashi et al. | |
| 2004/0022869 A1 | 2/2004 | Chen et al. | |
| 2004/0249219 A1 | 12/2004 | Saucy | |
| 2004/0265319 A1 | 12/2004 | Nishizono et al. | |
| 2006/0078604 A1 | 4/2006 | Kanios et al. | |
| 2007/0154534 A1 | 7/2007 | Sheitman et al. | |
| 2008/0113919 A1 | 5/2008 | Rose et al. | |
| 2009/0054623 A1 | 2/2009 | DeFrees | |
| 2009/0214607 A1 | 8/2009 | Lintner et al. | |
| 2010/0038141 A1 | 2/2010 | Johnson et al. | |
| 2010/0068141 A1 | 3/2010 | Kaushal et al. | |
| 2011/0158983 A1 | 6/2011 | Bascomb et al. | |
| 2011/0286993 A1 | 11/2011 | Jensen et al. | |
| 2012/0009125 A1 | 1/2012 | Lombard | |
| 2012/0172453 A1 | 7/2012 | Barres et al. | |
| 2013/0085283 A1 | 4/2013 | Serizawa et al. | |
| 2013/0245126 A1 | 9/2013 | Serizawa | |
| 2013/0296323 A1 | 11/2013 | Serizawa et al. | |
| 2014/0187646 A1 | 7/2014 | Serizawa | |
| 2014/0274967 A1 | 9/2014 | Boyle et al. | |
| 2014/0275091 A1 | 9/2014 | Serizawa et al. | |
| 2014/0275280 A1 | 9/2014 | Serizawa et al. | |
| 2014/0275281 A1 | 9/2014 | Serizawa et al. | |
| 2014/0275282 A1 | 9/2014 | Boyle et al. | |
| 2014/0275631 A1 | 9/2014 | Abril-Hörpel et al. | |

FOREIGN PATENT DOCUMENTS

| | | |
|---|---|---|
| EP | 1 447 083 | 8/2004 |
| EP | 1 717 315 | 11/2006 |
| JP | 55-020713 | 2/1980 |
| JP | 55-022632 | 2/1980 |
| JP | 06-192073 A | 7/1994 |
| JP | 2001-172171 | 6/2001 |
| JP | 2001-322929 A | 11/2001 |
| JP | 2004-010574 | 1/2004 |
| JP | 2005-060303 | 3/2005 |
| JP | 2006-063012 | 3/2006 |
| JP | 2007-075071 | 3/2007 |

(Continued)

OTHER PUBLICATIONS

Kikuchi (Effect of Geranylgeranylaceton on Cellular Damage Induced by Proteasome Inhibition in Cultured spinal Neurons, Journal of Neuroscience Research 2002, 69: pp. 373-381.*
Fujiki (Role of Proein Kinase C in Neuroprotective Efffect of Geranylgeranylacetone, a Noninvasive Inducing Agent of Heat shock Protein, on Delayed Neuronal Death Caused by Transient Ischemia in Rats, Journal of Neurotrauma, 2006, vol. 23, No. 7, pp. 1164-1178).*
U.S. Appl. No. 13/647,321, filed Oct. 8, 2012, Coyote Pharmaceuticals Inc.
U.S. Appl. No. 13/819,681, filed Feb. 8, 2013, Serizawa.
U.S. Appl. No. 13/943,606, filed Jul. 16, 2013, Serizawa.
U.S. Appl. No. 14/045,219, filed Oct. 3, 2013, Serizawa.
Barrero, et al., "Regio- and Enantioselective Functionalization of Acyclic Polyprenoide," J. Mex. Chem. Soc., (2006), 50(4):149-156.
Bestmann et al., "All-trans Geranylgeranyl Acetate and Geranylgeraniol, Recruitment Pheromone Components in the Dufour Gland of the Ponerine Ant *Ectatomma ruidum*," Naturwissenschaften, (1995), p. 334, Fig 2 and its legend, 82(12):334-336.
Boyle et al., "Osteoclast differentiation and activation", Nature (2003), 423(6937):337-342.
Bruestle et al., "Decline in Daily Running Distance Presages Disease Onset in a Mouse Model of ALS," Neuromolecular Med. (2009), 11(2):58-62.
Bruijn, "Aggregation and Motor Neuron Toxicity of an ALS-Linked SOD1 Mutant Independent from Wild-Type SOD1," Science (1998), 281:1851-1854.

(Continued)

*Primary Examiner* — Kathrien Cruz
(74) *Attorney, Agent, or Firm* — Foley & Lardner LLP

(57) ABSTRACT

Provided herein are methods for improving negative effects of ALS, AD, or ischemia, the methods comprising administering to a subject in need thereof a therapeutically effective amount of GGA, preferably present in the trans form, or a derivative thereof.

1 Claim, No Drawings

(56) References Cited

FOREIGN PATENT DOCUMENTS

| | | |
|---|---|---|
| JP | 2008-127296 | 6/2008 |
| WO | WO-99/66929 A1 | 12/1999 |
| WO | WO-99/67809 A1 | 12/1999 |
| WO | WO-02/03981 A1 | 1/2002 |
| WO | WO-02/080926 | 10/2002 |
| WO | WO-03/035052 | 5/2003 |
| WO | WO-2005/112915 | 12/2005 |
| WO | WO-2010/042841 | 4/2010 |
| WO | WO-2012/026813 | 8/2010 |
| WO | WO-2012/031028 A2 | 3/2012 |
| WO | WO-2013/023274 | 2/2013 |
| WO | WO-2013/052148 | 4/2013 |

OTHER PUBLICATIONS

Bucciantini et al., "Inherent toxicity of aggregates implies a common mechanism for protein misfolding diseases," Nature (2002), 416:507-510.
Burgess et al., "The Ligand for Osteoprotegerin (OPGL) Directly Activates Mature Osteoclasts", J. Cell Biol. (1999), 145(3):527-538.
CAPLUS printout of Grupta et al., Synthesis of five- and six-membered ring ketones with a long side chain for use as perfumes. Journal of the Indian Chemical Society. 1953, 30, 23-26.
CAPLUS printout of "Murakami et al.,Effect of synthetic acyclic polyisoprenoids on the cold-restraint stree induced gastric ulcer in rats. Japanese Journal of Pharmacology. 1983, 33,549-556."
CAPLUS printout of "Overman et al., A general method for the synthesis of amines by the rearrangement of allyic trichloracetimidates. 1,3 transposition of alcohol and amines functions. Journal of American Chemical Society. 1976, 98, 2901-2910."
CAPLUS printout of "Vig et al., Terpenoids. Part CXXXVI. Synthesis of geranylfarnesol. Indian Journal of Chemistry, Section B: Organic Chemistry Including Medicinal Chemistry. 1979, 17B, 31-33".
CAPLUS printout of Japanese Patent No. 4002114 or 2003238463.
Casez et al., "Dual-energy X-ray absorptionmetry for measuring total bone mineral content in the rat: Study of accuracy and precision", Bone and Mineral (1994), 26:61-68.
Cereda et al, "The Acetate of (Z)-4-Chloro-2-Methyl-2-Buten-A-OL Stereoselective Wittig Synthesis of a New Hemiterpenoid Synthon", Tetrahedron Lett. (1982), 23(21):2219-2222.
Chapelat, et al., "Biomimetic Chromanol Cyclisation: A common route to α-Tocotrienol and α-Tocopherol," Eur. J. Org. Chem., (2009), 2069-2076.
Chemical Abstract Registry No. 202828-37-3, indexed in the Registry File on STN CAS Online Mar. 19, 1998.
Chemical Abstract Service (CAS) STN Registry Database No. 1350042-87-3 [entered STN: Dec. 7, 2011].
Eisai Co., Ltd., "Patent Registration Completed for SELBEX Gastritis Use Treatment", News Release (1998).
Ernest et al, "Synthesis of the 7-Cis Isomer of the Natural Leukotriene D4," Tetrahedron Lett. (1982), 23(2):167-170.
Ferretti, "Perspectives of pQCT Technology Associated to Biomechanical Studies in Skeletal Research Employing Rat Models", Bone (1995), 17(4):3535-3645.
Fujiki et al., "Role of Protein Kinase C in Neuroprotective Effect of Geranylgeranylacetone, a Noninvasive Inducing Agent of Heat Shock Protein, on Delayed Neuronal Death Caused by Transient Ischemia in Rats," J Neurotrauma (2006), 23(7):1164-78.
Gittens et al., "Designing proteins for bone targeting," Adv Drug Deliv Rev., (2005), 57(7):1011-1036.
Gracias et al., "Synthesis of Fused Bicyclic Imidazoles by Sequential Van Leusen/Ring-Closing Metathesis Reactions", Org. Lett. (2005), 7(15):3183-3186.
Grinco et al. (2007) "Superacid-Catalyzed Cyclization of Methyl (6Z)-Geranylfarnesoates," Helv. Chim. Acta. 90:1223-1229.
Harada et al., "Neuroprotective Effect of Geranylgeranylacetone against Ischemia-Induced Retinal Injury", Molecular Vision, 2007, 13:1601-1607.

Heller et al., "1,3-Diketones from Acid Chlorides and Ketones: A Rapid and General One-Pot Synthesis of Pyrazoles", Org Lett (2006), 8(13):2675-2678.
Henderson et al., "Purified embryonic motoneurons," J Cohen and G P Wilkin (ed.), Neural Cell Culture (1995), 69-81.
Holmes et al., "Strategies for Combinatorial Organic Synthesis: Solution and Polymer Supported Synthesis of 4-Thiazolidinones and 4-Metathiazanones Derived from Amino Acids", J Org Chem (1995), 60:7328-7333.
Ichikawa et al., J.Chem. Soc. Perkin Trans. 1., (1993), 20:2429-2432.
Iguchi et al., "TDP-43 Depletion Induces Neuronal Cell Damage through Dysregulation of Rho Family GTPases," J. Bio Chem. (2009), 284(33):22059-22066.
Irvine et al., "Protein Aggregation in the Brain: The Molecular Basis for Alzheimer's and Parkinson's Diseases," Mol Med. (2008), 14(7-8):451-464.
Isshii, et al., "Retinal Ganglion Cell Protection with Geranylgeranylacetone, a Heat Shock Protein Inducer, in a Rat Glaucoma Model," Invest. Ophthalmol. Vis. Sci., (2003), 44(5):1982-1992.
Ito et al., "A medium-term rat liver bioassay for rapid in vivo detection of cacinogenic potential of chemicals," Cancer Science, (2003), 94(1):3-8.
Iuchi et al., "Oligomeric and polymeric aggregates formed by proteins containing expanded polyglutamine", PNAS (2003), 100(5):2409-2414.
Kato et al., "Synthesis and Pheromone Activities of Optically Active Neocembrenes and Their Geometrical Isomers, (E,Z,E)- and (E,E,Z)-Neocembrenes," J. Org. Chem. (1980), 45:1126-1130.
Katsuno et al., "Pharmacological induction of heat-shock proteins alleviates polyglutamine-mediated motor neuron disease", Proc. Natl. Acad. Sci. USA (2005), 102(46):16801-16806.
Kikuchi et al., "Effect of Geranylgeranylaceton on Cellular Damage Induced by Proteasome Inhibition in Cultured Spinal Neurons," J. Neuro Res., (2002), 69:373-381.
Kimmel et al., "The Effect of Recombinant Human (1-84) or Synthetic Human (1-34) Parathyroid Hormone on the Skeleton of Adult Osteopenic Ovariectomized Rats", Endocrinology (1993), 132(4):1577-1584.
Lacey et al., "Osteoprotegerin Ligand is a Cytokine that Regulates Osteoclast Differentiation and Activation", Cell (1998), 93:165-176.
Laval-Jeantet et al., "Dual-Energy X-Ray Absorptiometry of the Calcaneus: Comparison with Vertebral Dual-Energy X-Ray Absorptiometry and Quantitative Computed Tomography", Calcif Tissue Intl (1995), 56:14-18.
Li et al. A Novel Synthesis of Functionalized Allylsilanes. Organic Letters. 2004,6,1849-1852.
Li et al., Manganese (III)-Promoted Tandem Oxidated and Cyclization of beta-Keto Ester Derviatives of Terpenoids. Advanced Synthesis & Catalysis. 2011, 353, 1913-1917.
Liu, G.T., "Bicyclol: A novel drug for treating chronic viral hepatitis B and C," Medicinal Chemistry, (2009), 5:29-43.
Liu. et al., "Influence of geranylgeranylacetone on the expression of HSP70 in retina of rats with chronic IOP elevation," Int. J. Ophthamol., (2010), 3(1):28-31.
Martin-Murphy et al., "The role of damage associated molecular pattern molecules in acetaminophen-induced liver injury in mice," Toxicology Letters, (2010), 192:387-394.
Masuda et al., "Geranylgeranylacetone attenuates septic diaphragm dysfunction by induction of heat shock protein 70*," Crit. Care Med., (2003), 31(11):2585-2591.
Nagai, et al., "Neuroprotective effect of geranylgeranylacetone, a noninvasive heat shock protein inducer, on cerebral infarction in rats," Neuroscience Letters, (2005), 374:183-188.
Namba et al., "Suppression of Expression of Heat Shock Protein 70 by Gefitinib and Its Contribution to Pulmonary Fibrosis," PLoS One, (2011), 6(11):e27296.
Ooie et al., "Single Oral Dose of Geranylgeranylacetone Induces Heat-Shock Protein 72 and Renders Protection Against Ischemia/Reperfusion Injury in Rat Heart," Circulation (2001), 104:1837-43.
PCT International Preliminary Report on Patentability dated Sep. 12, 2014 in PCT Patent Application No. PCT/US2013/028073.

(56) References Cited

OTHER PUBLICATIONS

PCT International Preliminary Report on Patentability in PCT Patent Application No. PCT/US2013/028081, dated Sep. 12, 2014.
PCT International Search Report and Written Opinion dated Apr. 30, 2013 in PCT Patent Application No. PCT/US13/28073.
PCT International Search Report and Written Opinion dated Apr. 30, 2013 in PCT Patent Application No. PCT/US13/28075.
PCT International Search Report and Written Opinion dated Aug. 28, 2014 in PCT Patent Application No. PCT/US2014/026307.
PCT International Search Report and Written Opinion dated Aug. 7, 2014 in PCT Patent Application No. PCT/US2014/026263.
PCT International Search Report and Written Opinion dated Jan. 6, 2014 in PCT Patent Application No. PCT/US2013/062708.
PCT International Search Report and Written Opinion dated Jun. 18, 2013 in PCT Patent Application No. PCT/US13/28081.
PCT International Search Report and Written Opinion dated Jun. 3, 2014 in PCT Patent Application No. PCT/US2014/010385.
PCT International Search Report and Written Opinion dated Mar. 27, 2014 in PCT Patent Application No. PCT/US2013/035333.
PCT International Search Report and Written Opinion for PCT/US2014/026277, dated Jun. 27, 2014.
PCT International Search Report and Written Opinion dated Jan. 6, 2014 in PCT Appl. No. PCT/US2013/062708.
PCT International Search Report dated Jun. 2, 2013 in PCT Patent Application Serial No. PCT/US2013/025427.
PCT International Search Report dated Sep. 28, 2012 in PCT Appl. No. PCT/US2012/027147.
PCT International Search Report and Written Opinion dated Sep. 28, 2012 in PCT Application No. PCT/US2012/027147.
Perrin, et al., Neuroprotection by Hsp 104 and Hsp27 in Lentiviral-based Rat Modles of Huntington's Disease. Molecular Therapy. 2007, 15, 903-911.
Pezron et al., "Prodrug strategies in nasal drug delivery", Expert Opinion on Therapeutic Patents, (2002), 12(3):331-340.
Pfitzner et al., "A New and Selective Oxidtion of Alcohols," J.A.C.S. Communications to the Editor, (1963), 85:3027-3028.
Physician's Desk Reference for Ophthalmology 1982 Edition, published by Medical Economics Company, Inc., 112-114.
PubChem AC1NSMQO. Compound Summary (CID 5366012). (2E;6E,10E)-3,7,11,15-Tetramethyl-2,6,10,14-hexadecatetraenyl acetate. Mar. 27, 2005. [online]; [Retrieved from the Internet Jun. 6, 2013:].
PubChem Submission CID 5282199 titled "Geranylgeranylacetone" (Mar. 25, 2005) retrieved from internet http://pubchem.ncbi.nlm.nih.gov/summary/summary.cgi?cid=5282199.
Racine, R.J., "Modification of Seizure Activity by Electrical Stimulation: II. Motor Seizure," Electroencephalogr. Clin. Neurophysiol., (1972), 32:281-294.
Ross & Poirier, "Protein aggregation and neurodegenerative disease," Nat Med. (2004), S10-S17.

Schenk et al., "Quantitative Morphometric Evaluation of the Inhibitory Activity of New Aminobisphosphonates on Bone Resorption in the Rat", Calcif.Tissues Int (1986), 38:342-349.
Simonet et al., "Osteoprotegerin: A Novel Secreted Protein Involved in the Regulation of Bone Density", Cell (1997), 89:308-319.
Sorrell et al., "A Regiospecific Synthesis of 1,4-Disubstituted Imidazoles", J Org Chem (1994), 59:1589-1590.
Sreekumar et al, "A Direct Synthesis of 2-Trisubstituted Allylic Alcohols via the Wittig Reaction", J. Org. Chem. (1980), 45:4260-4262.
Stotter et al., "α-Halocarbonyl Compounds. II. A Position-Specific Preparation of α-Bromo Ketones by Bromination of Lithium Enolates. A Position-Specific Introduction of α,β-Unsaturation into Unsymmetrical Ketones", J Org Chem (1973), 38(14):2576-2578.
Suzuki et al., "Geranylgeranylacetone ameliorates ischemic acute renal failure via induction of Hsp70," Kidney Int (2005), 67:2210-20.
Tanaka et al., "Protective role of HSF 1 and HSP 70 against gastrointestinal diseases," Int. J. Hyperthermia, (2009), 25(8):668-676.
Tanito et al., "Cytoprotective Effects of Geranylgeranylacetone against Retinal Photooxidative Damage," J Neurosci (2005), 25(9):2396-404.
Tokumasu et al. "Synthesis of rac-hippospongic acid A and revision of the structure", JCS Perkin Trans. (1999), 1(4):489-496.
Van Leusen et al., "Base-Induced Cycloaddition of Sulfonylmethyl Isocyanides to C,N Double Bonds. Synthesis of 1,5-Disubstituted and 1,4,5-Trisubstituted Imidazoles from Aldimines and Imidoyl Chlorides", J. Org. Chem. (1977), 42(7):1153-1159.
Vig., et al., Stereospecific synthesis of (+)-2,3-Dihydro-6(E)-farnesol. Indian J. Chem., Section B: Org. Incl. Med. Chem., (1979), 18B:31-38.
Vik et al., "Screening of Terpenes and Derivatives for Antimycobacterial Activity; Identification of Geranylgeraniol and Geranylgeranyl Acetate as Potent Inhibitors of *Mycobacterium tuberculosis* in vitro," Planta Med., (2007), p. 1411, Fig. 1, compound 1, 73(13):1410-1412.
Wang et al., "Bisphosphonate-decorated lipid nanoparticles designed as drug carriers for bone diseases," J Biomed Mater Res. A., (2012), 100(3):684-693.
Wang et al., "Protein Aggregation and Protein Instability Govern Familial Amyotrophic Lateral Sclerosis Patient Survival", PLoS Biology (2008), 6(7):1508-1526.
Wasserman et al., "Mechanism of the Robinson-Gabriel synthesis of oxazoles", J Org Chem (1973), 38(13):2407-2408.
Yasuda et al., "Neuroprotective effect of a heat shock protein inducer, geranylgeranylacetone in permanent focal cerebral ischemia," Brain Res (2005), 1032:176-82.
Yu et al., "Synthesis of Farnesol Isomers via a Modified Wittig Procedure", Organic Letters, (2005), 7(22):4803-4806.

\* cited by examiner

TREATING NEURODEGENERATIVE DISEASES WITH GGA OR A DERIVATIVE THEREOF

CROSS REFERENCE TO RELATED APPLICATION

This application claims priority to U.S. provisional application No. 61/711,162, filed Oct. 8, 2012, the contents of which is included herein in its entirety by references.

FILED OF INVENTION

This invention relates to improving negative effects of amyotrophic lateral sclerosis (ALS), alzheimers disease (AD), or ischemia by administering geranylgeranyl acetone (GGA) or a derivative.

STATE OF THE ART

Amyotrophic lateral sclerosis (ALS) is a progressive neurodegenerative disorder that causes muscle weakness, disability, and eventual death, with a median survival of three to five years.

Incidence rates for ALS in Europe and North America range between 1.5 and 2.7 per 100,000/year, while prevalence rates range between 2.7 and 7.4 per 100,000; there is no definite racial or ethnic predisposition. Overall, the male to female ratio is about 1.3 to 1.5, with higher male predominance at younger age and near equality at older ages. The incidence of ALS increases with each decade, especially after age 40 years, and peaks in the seventh to eighth decade. In the United States, about 7000 new cases of ALS are diagnosed each year. The incidence and mortality rates of ALS have been slowly increasing over decades. Part or all of this increase in ALS incidence may be due to longer life expectancy.

Worldwide, approximately 90% of cases of ALS are sporadic (SALS), with the remaining 10% familial (FALS) and caused by mutations in one of several genes. SALS is likely linked to alterations in complex gene systems, forming genetic risks factors rather than a direct cause of ALS. In FALS there is often Mendelian inheritance and high penetrance, with most cases following an autosomal dominant inheritance pattern.

The genetic etiology of nearly half of FALS is unknown. Approximately 15 genetic mutations have been identified as causes of ALS, although the causative nature of the gene mutations is still unknown. Among these, mutations in 72C9ORF72, SOD1, TDP43, FUS, ANG, VCP, OPTN are associated with typical ALS; the remainder are associated with unusual phenotypes or small numbers of kindreds. The most common mutation appears to be C9ORF72 (FTD-ALS) repeat expansion accounting for 24 to 47% of FALS, while the second most common gene mutation, SOD1, accounts for about 12% to 20% of FALS. The most common mutation in North America is the A4V, which is associated with a very aggressive form of ALS accounting for 50% of SOD1 patients.

The central pathology of ALS is atrophy and death of anterior horn cells and cortical motor neurons, and may affect other neuronal populations, particularly frontal cortical neurons, leading to concurrent frontotemporal dementia. Differences in site and segment (cranial, cervical, thoracic, or lumbosacral) of onset, pattern and speed of spread, and the degree of upper and/or lower motor neuron dysfunction produce a disorder that is remarkably variable between individuals. The initial clinical manifestation of ALS may occur in any body segment (bulbar, cervical, thoracic or lumbosacral) and may manifest as upper motor neuron or lower motor neuron symptoms or signs. Asymmetric limb weakness is the most common presentation of ALS (80%), followed by bulbar onset, respiratory muscle weakness, or generalized weakness. The frequency of frontotemporal executive dysfunction in patients with ALS reportedly occurs in 35-51% of patients with ALS. The median survival from the time of diagnosis is three to five years; however, about 10% of patients live 10 years or more. A principal difficulty in the diagnosis and management of ALS is the absence of clinical biomarkers, which contributes to a diagnostic delay of 9 to 12 months and to initial false-negative diagnosis in up to 10% of cases.

The complex pathophysiology of ALS suggests that it is a multifactorial disorder and presents many potential therapeutic targets. In recent years, a large number of experimental therapies and neuroprotective agents with varying mechanisms of action have been tested clinically (including agents targeting excitotoxicity, neurotrophic agents, immunomodulators, agents targeting oxidative stress, anti-apoptotic compounds and nutritional supplements) and have failed. Although several drugs (such as creatine, celecoxib, IGF-1, CNF, gabapentin, topiramate, lamotrigine, xaliproden, minocycline, thalidomide, valproate, vitamin E) gave positive results in preclinical animal studies, none of these compounds, when tested in humans, significantly prolonged survival or improved quality of life of ALS patients.

A range of mechanisms have been implicated in the initiation and propagation of the neurodegenerative process in ALS that may not be mutually exclusive and include excitotoxicity, oxidative stress due to free radical generation, protein misfolding, protein aggregation, neurofilament aggregation, mitochondrial dysfunction, proteasomal dysfunction, aberrant growth factor signaling, apoptosis, impaired axonal transport, microinflammatory process and glial activation.

Numerous agents with potential neuroprotective effects that have been investigated include those from the categories of free radical scavengers, anti-excitotoxic agents, apoptosis inhibitors, anti-inflammatory agents, neurotrophin factors, metal ion chelators, ion channel modulators and gene therapies.

Two preclinical and clinical strategies in ALS drug development are: 1) preventing death of the motor neuron soma by pharmacologically targeting the neuron and 2) supporting motor neuron health indirectly by targeting the biology of ambient glia. A third strategy gaining momentum in preclinical studies reconceptualizes ALS as a cytoskeletal disease and targets degenerative processes involving neuromuscular junctions (NMJs). It is based on the fact that motor neuron cell death only happens near the end of an extensive clinical disease and thus likely is a final consequence of other neuronal processes, whereas NMJ damage occurs in the early stages of disease progression, long before motor neuron loss. ALS can be thought of as a progressive distal axonopathy that follows NMJ denervation but precedes both neuronal degeneration and the onset of clinical symptoms.

Recently, several new agents have reportedly shown evidence of benefit in Phase 2 trials. Particularly, dexpramiprexole, an amino-benzothiazole, through actions involving mitochondria, tirasemtiv (CK-2017357), a fast skeletal muscle troponin activator, and NP001, a regulator of macrophage function.

Only one therapeutic with similar targets has been tested in clinical trials for ALS. Arimoclomol is a drug that upregulates molecular chaperones in cells. Pre-symptomatic administration as well as treatment with arimoclomol at disease onset extended the life span of SOD1 G93A by approximately 5 weeks. In a Phase 2a open label clinical trial run, a reduction in decrease of ALSFRS-R, vital capacity, total body weight and body mass index was observed when compared with a historical control. No other clinical trial has been performed investigating HSP70 induction or modulation of GGTase in ALS.

Despite over 30 phase II and phase III clinical trials of promising agents, riluzole remains the only evidence-based disease-modifying drug for ALS. An American Academy of Neurology practice guideline, published in 2009, recommended riluzole, a benzothiazole analog, as safe and effective for the slowing of progression in ALS, though only to a modest degree and without effect on motor function. The gain in survival is approximately 11% or 3 months. The precise mode of action of riluzole is unknown. It appears to be a low potency, nonspecific modulator of multiple pharmaceutical targets that include the inhibition of presynaptic glutamate release, inactivation of voltage-dependent ion channels, prevention of protein aggregation, and more recently, neuroprotection via an astrocyte dependent mechanism leading to enhanced glutamate reuptake rather than by regulating glutamate release. Due to the inevitably progressive nature of ALS, symptomatic, preservation of quality of life, and palliative treatments contribute significantly to clinical management of patients with ALS, regardless of riluzole treatment.

Extension of survival over that achieved by riluzole is considered a minimally acceptable result that must be accompanied by a slowing of disease progression, as measured by comparing pretreatment and 6-12 months of treatment ALSFRS-R scores, and that delays onset of ventilator assistance in both familial and sporadic ALS. Also, as a minimum, the drug must be safe and tolerable to the majority of eligible patients. The drug would be taken twice daily mixed in food or drink with little to no pharmacokinetic interference.

The upregulation of HSP70, for example, has been reported i with riluzole and arimoclomol. HSP70 is effective with its co-chaperone HSP40 that features a CAAX prenylation motif and which is required for binding of GGT. Pleiotrophic effects of these drugs, can be observed although in most, the mechanism of action has not been determined.

Modulation of prenylation can also be a part of the mechanism of action of statins and bisphosphonates. These drugs block the cholesterol synthesis pathway, an intermediate of which is GGPP, the main substrate of GGTase. Inhibition of prenylation has been invoked as an explanation of the anti-inflammatory effects of statins and it is conceivable that this results in neuroprotection in ALS. Furthermore it has been reported that statins are able to improve clearance of misfolded proteins in a model of Alzheimer's disease by modifying prenylation. However, to our knowledge, these pharmaceutical approaches have not been investigated for drug development in ALS.

SUMMARY OF INVENTION

Provided herein are methods for improving negative effects of ALS, AD, or ischemia, the methods comprising administering to a subject in need thereof a therapeutically effective amount of GGA, preferably present in the trans form, or a derivative thereof. As used herein, a therapeutically effective amount refers to an amount of GGA or a derivative thereof that can improve the negative effects of ALS, AD, or ischemia in a subject or an in vitro or in vivo model thereof. As also used herein, the term "treatment" or "treating" means any treatment of a disease or condition in a patient, including one or more of:

preventing or protecting against the disease or condition, that is, causing the clinical symptoms not to develop, for example, in a subject at risk of suffering from such a disease or condition, thereby substantially averting onset of the disease or condition;

inhibiting the disease or condition, that is, arresting or suppressing the development of clinical symptoms; and/or relieving the disease or condition that is, causing the regression of clinical symptoms.

Modes of administering an agent, such as GGA or a derivative thereof, in accordance with the present invention, is well known to the skilled artisan and/or will be apparent to the skilled artisan upon reading this disclosure. In a preferred embodiment, the GGA or the derivative thereof is administered as a 7 day patch.

DETAILED DESCRIPTION OF THE INVENTION

Provided herein are methods related to modulation of the activity of small GTPases by influencing their prenylation to stabilize the cytoskeleton in neurites for the treatment of ALS. In some embodiments, these methods utilize CNS-102, which is a structural mimic of the prenylation substrate GGPP. Prenylation influences multiple signaling pathways that modulate functions such as cell movement, motility, cell growth, cell survival, and expression of HSPs.

In some embodiments, the compounds utilized herein extend survival and improve quality of life by inhibiting the disease progression and demonstrate improvement in the slope of the ALSFRS-R scores measured over a 6-12 month period. In some embodiments, the compounds utilized herein are administered once daily in food or drink, or delivered by a 7-day patch.

In some embodiments, the compounds utilized herein have the following chemical properties for optimal CNS penetration and bioavailability: molecular weight <400, lack ionization at physiological pH, lipophilic, polar surface area estimated at 60-90 $Å^2$, minimal hepatic first pass effect, i.e., no significant CYP2D6 metabolism. Additionally, the compound is well absorbed and have high absolute oral bioavailability in order to minimize the total amount of drug needed and to attenuate side effects or interactions with other drugs. Additionally advantages would include minimal compound that is bound to plasma proteins over the clinical concentration range; pharmacokinetics that are linear over the therapeutic dose range, and PK given every 24 hours for effective single daily dosing.

Embodiments including certain compound characteristics are tabulated below.

| Compound Properties | Minimum Acceptable Result | Ideal Result |
|---|---|---|
| Primary Drug Indication | Treatment to extend survival, slow progression and delay onset of ventilator assistance in sporadic and familial ALS | Treatment to extend survival and halt neurodegeneration in sporadic and familial ALS |
| Patient Population | Adults with ALS | Adults with ALS |
| Delivery Mode | Oral | Oral or Patch |
| Treatment Duration | Chronic | Chronic |
| Regimen | 2x/day | 1x/day oral or 1x/week patch |

-continued

| Compound Properties | Minimum Acceptable Result | Ideal Result |
|---|---|---|
| Efficacy | Extends survival by ≥20%, slows progression as measured by the slope of ALSFRS-R and delays onset of ventilator assistance in sporadic and familial ALS. Safe and well tolerated | Extends survival ≥40 % and delays onset of ventilator assistance. Inhibits neurodegeneration and stabilizes the disease. Demonstrates improvement in slope of ALSFRS-R over a 9-month period. Safe and well tolerated |

In these regards, 5E,9E,13E-geranylgeranylacetone (trans GGA or CNS-102), which is an isomorph of geranylgeranyl pyrophosphate (GGPP), the prenylation substrate for geranylgeranyl transferase, (GGTase I) exhibits neuroprotective activity capable of supporting different classes of neurons threatened by a variety of endogenous genetic or exogenous pharmacologic stressors. In vitro, CNS-102 protects neurites from toxicity caused by an inhibitor of GGTase I. Systemic CNS-102 upregulates expression of several HSP genes in the brain cortex and hippocampus, with concomitant induction of HSP expression in brain cortex. It also provides neuroprotection in the hippocampus against excitotoxicity induced by kainic acid. In the superoxide dismutase 1 (SOD1) mouse model of ALS, CNS-102 significantly prolonged survival, improving clinical scores, neurological scores, and computerized assessment of gait parameters, suggesting that CNS-102 can also be effective in delaying onset or progression of symptoms.

It is contemplated that that compounds such as CNS-102 and analogs based on its scaffold can modulate geranylgeranyltransferase I (GGTase I) activity. This in turn is thought to regulate prenylation of small G-proteins such as Rho, Rac and Cdc42 and affect their activities on various aspects of neuronal development, including neurite outgrowth and differentiation, axon pathfinding, and dendritic spine formation and maintenance. Furthermore, it is contemplated that compounds based on the CNS-102 scaffold can induce HSP expression such as HSP70, and lead to inhibition of cytotoxicity-induced neuronal cell death during the pathological process of ALS. In some embodiments, treatment with CNS-102 or analogs may provide neuroprotection by inhibiting apoptosis and promoting regeneration of degenerating motor neurons, thus improving survival and behavioral outcome measures of ALS patients. Moreover, since some of the aforementioned molecular and cellular pathological features of ALS are shared by AD and HD patients, it is contemplated that our compounds can also benefit the treatments of other neurodegenerative diseases.

A hallmark feature of ALS is muscle weakness caused by denervation, dysfunction and degeneration of motor neurons. While other muscle types respond to stress and damages by up-regulation of heat shock proteins such as HSP70, motor neurons are lacking the response of HSP70 upregulation, probably rendering them more vulnerable to a variety of insults.

A key component of the proposed mechanism of action of CNS-102 is to up-regulate HSP70 activity, therefore inducing a cytoprotective and anti-apoptotic response in neurons. Post-translational protein prenylation mediated by GGTase I, regulates activities of small GTPases such as Ras, Rap1, and Rho (Rho, Rac, Cdc42), modulating a signal cascade that leads to activation of HSP70. These GTPases are involved in multiple cellular processes, including proliferation, apoptosis, cell morphogenesis and metastasis in a multitude of tissues. GGTase I is one of the two major enzymes that catalyze the attachments of isoprenoid lipids to the C-termini carrying CaaX motif of proteins. Despite some reports that GGTase I is dispensable for membrane association and/or forming GTP-bound small GTPases in non-neuronal cells, it is considered that GGTase I dependent prenylation is required for activating Rho GTPases at the cell membrane in neuronal cells. As an example, one strategy for modulating Rho GTPase activities has been the inhibition of GGTase I in the treatment of cancer.

GGA has been reported to be an inducer of HSP70 activity conferring neuroprotection in vitro in models of Parkinson's disease and heat injury such as burns. GGA also proved to be neuroprotective in vivo by inducing HSP70 in models of ischemia and glaucoma. In a model of proteasome impairment in cultured motor neurons, simulating conditions that may be found in ALS, GGA induced the expression of HSP70 and was found to be neuroprotective. Recently, it was shown in motor neurons of the SOD1 G93A model that a co-inducer of the heat shock response, arimoclomol, increased innervation, end plate size, and activity of cholinergic enzymes and reversed muscle fiber transformation, compared to control groups. This was accompanied by a concomitant increase of HSP70 expression. Interestingly, injection of human recombinant HSP70 protein in SOD1 mice delayed the peripheral muscle denervation.

Upregulation of HSP70, a measurable outcome of prenylation, has been demonstrated to be beneficial in several models of neurodegeneration and also in vivo in models of motor neuron disease and in mouse models of ALS. In some embodiments, treatment with CNS-102 analogs improve several outcome measures (life span, motor performance, muscle strength, motor neuron denervation, neuropathology in brain and spinal cord) in the SOD1 G93A mouse model of ALS. CNS-102 shows efficacy at nanomolar levels and exhibits excellent bioavailability and brain penetration, which makes it a suitable candidate for treatment in human patients with ALS.

Biomarkers

Without being bound by theory, the mechanism of action of CNS-102 is postulated to be prenylation of G proteins and induction of HSPs. It has been determined that in murine Neuro2A cells and in a rat kainic acid (KA) induced neurotoxicity model, CNS-102 increases expression of HSPs. Expression of HSP70 and HSP90 was found in the neuroblastoma cell study, while in the neuroprotection study, increased expression of HSP70 in hippocampus and cerebral cortex was observed in addition to upregulation of HSP60, HSP70, and HSP90.

Since a therapeutic effects of CNS-102 in ALS relate to intracellular actions of HSPs, changes in intracellular levels of HSP70 can be relevant as a biomarker along with HSP27 and HSP90. Circulating white blood cells are the most conveniently accessible cells and two small clinical trials have reported transient induction of HSP70 and HSP90 in PBMCs following a single dose of geranylgeranylacetone (GGA) or a GGA derivative. HSP70 is also detectable in cerebrospinal fluid (CSF) where it presumably is derived from brain and spinal cord tissue. Elevation has been reported in relationship to ischemia and seizure. CSF HSP70 is advantageous in that changes are more likely to reflect events in the CNS, but would only be considered if a suitable peripheral biomarker could not be established. Studies with ex vivo human PBMCs, would determine if changes in PBMC HSP are detectable following drug exposure, and if these correlate with changes in CNS HSP expression. If HSP induction is insufficient in PBMC, skin or muscle can serve as alternative tissue sources for assessment of HSP induction in clinical trials. Events in skeletal muscle may be of greater relevance for ALS, since increasing muscle HSP70 correlated to rescue of SOD1 mice. In some embodiments, both skin and muscle are less attractive than blood because biopsy is inherently more invasive than phlebotomy, increasing discomfort for subjects and usually limiting sampling to one or two post-treatment time points.

Preclinical Studies

The following experimental evidence support CNS-102's activity as a neuroprotective agent capable of protecting different classes of neurons threatened by a variety of endogenous genetic or exogenous pharmacologic stressors. 1) In vitro, CNS-102 protects neurites on neuroblastoma cells from toxicity caused by an inhibitor of geranylgeranyl transferase. 2) Systemic CNS-102 has also provided neuroprotection in the hippocampus against locally injected kainic acid. This benefit is prolonged with peak protection at 72 hours following a single oral dose. 3) CNS-102 significantly prolonged survival in the SOD1 mouse model of ALS and improved clinical scores, neurological scores, and computerized assessment of gait parameters reaching statistical superiority over scores in vehicle treated mice. Successful prolongation of survival with CNS-102 in this well recognized murine model of ALS is the chief justification for the proposed use of CNS-102 as a lead compound for the indication of ALS.

In the SOD1 mouse model of ALS (N=16/treatment, randomized design), daily treatments of CNS-102 and riluzole each produced a statistically significant improvement in median survival time compared to the vehicle control group, and CNS-102 outperformed riluzole by 50%, although the difference between the two drug treatment groups, when compared directly, was not statistically significant at p=0.05. Analyses were conducted using PROC LIFEREG in SAS.

| Group | Increase over vehicle | p-value |
|---|---|---|
| CNS-102 | 9% | 0.0007 |
| riluzole | 6% | 0.0149 |

Additionally, three neurological function outcomes were chosen for analysis from those measured on a 'cat-walk' at irregular intervals over the duration of the study; stride length (cm), run duration (s), and swing speed (cm/s). Prior to post-natal day (P) 119, there were only small differences between treatment group averages. Two specific subsets of data were collected for all of the surviving animals: one over a 2-day period from P119 to P121 (21 animals; 12 CNS-102, 9 vehicle), and the other over the interval of P122 and P127 (13 animals; 10 CNS-102, 3 vehicle).

By P119, the progression of the disease had both increased the measured differences in averages between treatments and removed significant but unequal fractions of each treatment group. This non-random censoring of the treatment group data precluded using standard comparative statistical methods such as the t-test due the unverifiable compliance of the remaining data with required statistical test assumptions. Consequently, a Monte Carlo estimate of the p-value of the treatment differences was constructed using the bootstrap method. The p-value for each difference in drug-minus-vehicle averages is calculated by comparison to the distribution produced from bootstrap results of 10 MM iterations. These are shown in the table below.

| | Comparison of Averages | | | |
|---|---|---|---|---|
| Age | P120 ± 1 | | P124 ± 3 | |
| Metric | CNS-102-vehicle | p-value | CNS-102-vehicle | p-value |
| Stride Length | 1.46 | 0.031 | 1.87 | 0.0062 |
| Run Duration | −1.68 | 0.034 | −1.49 | 0.0077 |
| Swing Speed | 14.58 | 0.017 | 11.70 | 0.0206 |

Furthermore, these p-values did not suffer significant change when the minus-one jacknife procedure of Quenouille and Tukey was applied to the data. This demonstrated that no single animal unduly influenced the construction of the reference distribution, thereby bolstering confidence in these p-value estimates.

These results are taken as proof that CNS-102 has the activity required for a medicinal chemistry synthesis program, and the scaffold from which CNS-102 is constructed is a valid framework from which to propose new structures. Clearly, the fact that all three neurological metrics show significantly better outcomes compared to vehicle, indicates that CNS-102 not only prolongs survival but also slows the symptomatic progression of the disease.

Primary Screening Assay—HSP70 Expression

It is contemplated that compounds useful according to the present methods can be identified by screening pools of compounds for their effect on prenylation. It has been found that CNS-102 I modulates GGTase I activity as detected by a fluorescent peptide, dansyl-GCVLL. CNS-102 treatment can lead to increased prenylation of important signaling molecules, whose activation in turn results in unregulation of HSP protein expression. In some embodiments, increase in HSP70 is chosen as the primary screening assay target for identifying GGA derivatives particularly suitable for the methods provided herein.

HSP70 expression in neuro2A cells treated with CNS-102 analogs are examined, using Western blot analysis. An increased expression of HSP70 will indicate the candidate molecule has the prerequisite activity. This assay has a Z factor of −0.9 and a CV of 11% for CNS-102 at 1 nM to 100 nM.

A commercial GGA related compound, teprenone, which preserves motor neurons, has been shown to regulate HSP expression at the level of heat shock transcription factor 1 (HSF1). It can bind to HSP70 to relieve the inhibition of HSF1 and allow the latter to translocate to nucleus and activates new HSP proteins. It is contemplated that the consequence of increased HSF1 nuclear translocation upon CNS-102 treatment, notably the upregulation of HSP70, can be observed.

Secondary Assay—Neurite Outgrowth

Neurite outgrowth in neuro2A neuroblastoma cell lines has been widely used as a cellular model for compounds screening in the CNS drug discovery and research. IN some embodiments, the effects of CNS-102 analogs on neurite outgrowth is determined. Cells will be pre-treated with candidates and then subjected to a challenge with GGTase I inhibitor GGTI-298. Retinoic Acid will be added to start the differentiation of these cells. This will identify analogs that protect neurite outgrowth, which is known to be important for establishing synaptic connections and neuronal functions. This assay has a Z factor of 0.4 and a CV of 11% for CNS-102 at 10 nM to 1 μM.

Confirmatory Assay—Rat Neuroprotection Model

Excitotoxicity has been considered as one of the major causes for neuron loss in ALS. A probable cause for excitotoxic neuron death is excess glutamate around the synapses, due to impaired glutamate reuptake capabilities. Intra-cerebral infusion of kainic acid is a well-established and robust model for excitotoxic neuron death that has been used to investigate excitotoxicity for over fifty years. Compounds are tested, e.g., at two concentrations and compare to a vehicle control in a model that quantifies neuron loss in the CA3 area of the hippocampus. Such tests can evaluate blood brain barrier penetration and select compounds that provide neuroprotection from excitotoxic damage.

ALS Disease Model—SOD1 Mouse Model

Survival studies and behavioral tests will be performed in the SOD1 G93A model of ALS. This transgenic mouse harbors a point mutation (G93A), found in familial ALS, in the gene encoding for superoxide dismutase 1 (SOD1). This very well characterized mouse model is widely used in ALS research. SOD1 G93A mice exhibit all of the histopathological hallmarks of familial and sporadic ALS that are observed in human patients. Motor neuron death in the ventral horn of the spinal cord and loss of myelinated axons in the ventral motor roots lead to paralysis and muscle wasting. Mice initially develop normally and gain weight until approximately 100 days of age. At this point, weight loss (which is usually defined as the onset of disease), muscle weakness, and gradual paralysis start at the hind limbs and muscle wasting start to appear. Maximum median life span is usually between 129-170 days depending on the background strain. This means that drug efficacy studies using this model can be performed within a relatively short time frame of 4-5 months. To rigorously test the efficacy of candidates in this mouse model, neurological scores are monitored, and motor scores, life span, body weight and mice tested in a battery of behavioral paradigms suitable for motor assessment.

Observed Activity in Disease Models

Previous studies using GGA in a mouse model of spinal and bulbar muscular atrophy (SBMA) have shown that GGA can induce expression of a group of HSPs (HSP70, HSP90 and HSP105) in various tissues including CNS, and inhibit neuronal cell death in cell culture and in vivo. Moreover, it has been demonstrated that GGA can reduce proteasome inhibitor induced neurotoxicity in cultured spinal neurons at low concentration (1 nM-100 nM). As the proteasome has been implicated in the pathogenic process of ALS, application of CNS-102 may be effective in ALS as well.

It has also been reported, that depolarization and BDNF application can activate GGTase I and promote dendritic morphogenesis of cultured hippocampal neurons. Additionally, prenylation of target protein Rac1 by GGTase I has been linked to neuron development. These conclusions are supported by the observation that overexpression of Rac1 bearing prenylation site mutations or deletion can abolish GGTase I dependent neuronal morphological development. Therefore, another function that is useful for a compounds is contemplated to be induction of prenylation of protein targets that are important in dendrite morphogenesis.

Chemical Structure

The chemical structure of CNS-102 is shown. We have characterized CNS-102 (MW 330) by $^1$H NMR, LC, and ESI mass spectrometry and no evidence of cis isomer was found. CNS-102 is a colorless oil with a density of 0.87 g/mL, having a calculated topological polar surface area (tPSA) of 17.07 and a calculated Log P of 7.61. Because CNS-102 is lipophilic, it has little intrinsic water solubility. Such can enable CNS-102 to cross the blood brain barrier.

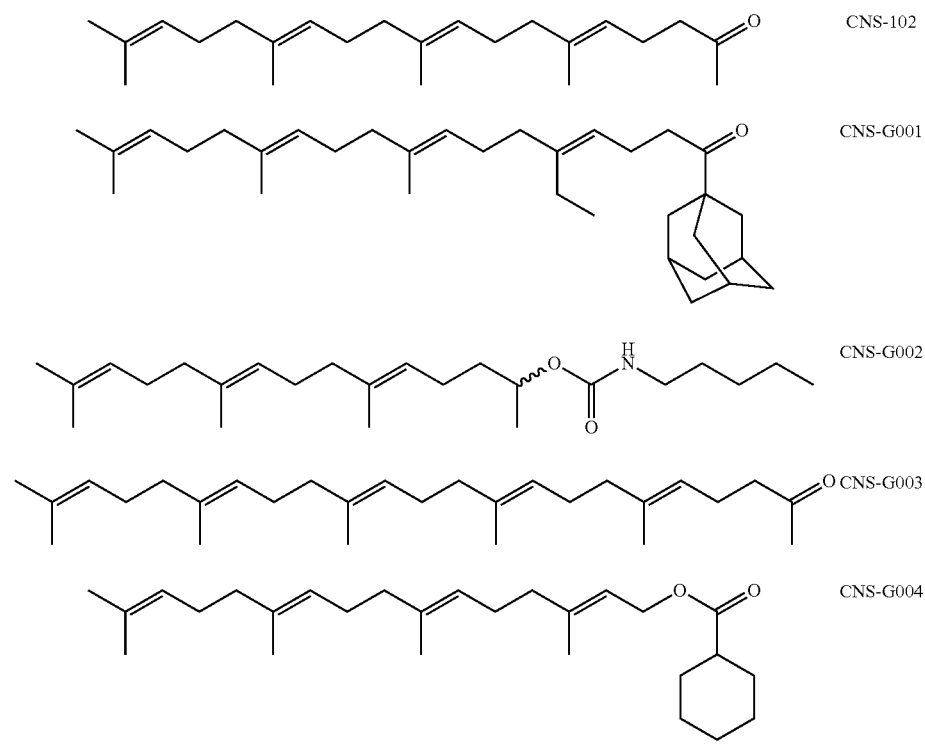

Structures Tested Based on CNS-102 Scaffold

Structures Tested Based on CNS-102 Scaffold

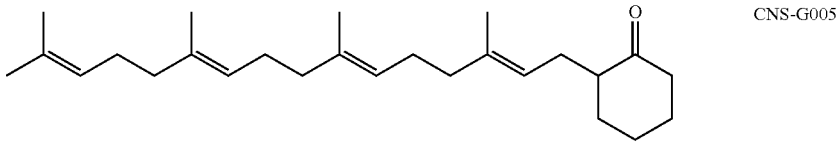

CNS-G005

Screening Strategy and Bioactivity Assays

A preliminary screen and quantitative performance evaluation, and a confirmatory neuroprotective assay are developed from a model of motor neuron dysfunction in a PNS cell line. The screen and initial quantitative performance evaluation is conducted on a single biomarker, HSP70, which has been found to be broadly implicated to neuroprotection based on the rationale that induction of HSP70 is a necessary property of the potential treatment for ALS.

The overall strategy, therefore, is to use a sequence of assays, each of which is targeted to address a specific aspect of the disease with the goal of identifying candidates having multiple therapeutic capabilities. These assays are chosen such that a failure to perform at any stage is expected to be fatal to the candidate's suitability as a viable ALS treatment. To this end, the following four therapeutic capabilities and corresponding assays were chosen as shown in the list below. The advancement criteria, as well as assay design where relevant, are also presented.

1. In some embodiments, the candidates increase HSP70 expression in target cells. The initial screen (pass/fail, Assay 1a) and quantitative evaluation ($EC_{50}$, Assay 1b) of candidates will use a HSP70 expression assay by Western blot on cellular extracts of treated Neuro2A cells. The screen, Assay 1a, is conducted at a single concentration, requiring a specific level of activity to pass into Assay 1b, the quantitative dose/response determination of the $EC_{50}$. Only those candidates having an $EC_K$, below 10 nM would be promoted to Assay 2.
2. In some embodiments, the candidates increase neuronal cell health/growth in the presence of specific inhibitors of GGTase I. The ability of candidates to promote neurite extension will be measured on Neuro2A cells to model whole-cell activities important to synaptic connections and neuronal function. Candidates showing >200 cells with outgrowth would be promoted to Assay 3.
3. In some embodiments, the candidates provide protection to nerve tissue from excitotoxins. Neuroprotection afforded by candidates that have passed the first two assays will be determined on rat hippocampal neurons facing kainic acid induced damage. This is the final animal model before the ALS disease model and candidates that provide >50% protection would be tested in the disease model.
4. In some embodiments, the candidates increase median survival time by 25% and improve neurological performance compared to control. This confirmation will be determined in the SOD1 mouse model.

| Bioactivity Assays | | | |
|---|---|---|---|
| # | Assay | Throughput | Advancement Criteria |
| 1a 1b | HSP70 Expression | 30/ per 2 weeks | Promote if ≥1.5X PBS at 1 µM $EC_{50}$ ≤ 10 nM |
| 2 | Neurite Outgrowth | 20 per 2 weeks | Promote if ≥200 cells at 10 nM |
| 3 | Rat Neuroprotection Model | 8-12 per month | Promote if ≥50% protection at 2 or 20 mg/kg |
| 4 | SOD1 Mouse ALS Model | 3 per 6 months | 25% increase in survival. Improved clinical and neurological scores. |

In some embodiments, the assays were arranged in a specific order to maximize the early throughput with minimal effort being expended on the more labor-intensive assays, which maximizes overall throughput. This organization provides a "fail-early" probability to those compounds that have lower likelihood of clinical success, which removes them as early as possible from further consideration. Those candidates that pass through the assay cascade will be tested in the SOD1 mouse ALS model for confirmation.

| Correlation of Assay Cascade Results | | | | |
|---|---|---|---|---|
| Assay | 1a & 1b | 2 | 3 | 4 |
| Name | HSP70 Expression | Neurite Outgrowth | Rat Neuroprotection | SOD1 Mouse Model |
| Metric | HSP70 by Western Blot | Cell count relative to negative control | % Protection | Survival and clinical scores |
| Promotion Criteria | ≥1.50 × PBS | ≥2.00 @ 10 nM | ≥75% | n/a |
| CNS-102 | 2.05 × PBS | 2.00 | 40% | 9% increase in survival |
| CNS-G001 | 2.00 × PBS | 1.79 | 37% | n/a |
| CNS-G002 | 1.26 × PBS | 1.79 | 0% | n/a |
| CNS-G003 | 2.78 × PBS | 2.74 | 82% | n/a |
| CNS-G004 | 2.34 × PBS | 2.61 | 76% | n/a |
| CNS-G005 | 2.78 × PBS | 2.28 | 83% | n/a |
| Correlation | n/a | 78% | 86% | n/a |

In some illustrative embodiments, CNS-G002, shows activity below the promotion threshold in the next assay downstream and showed no observable neuroprotective activity under the test conditions in the kainic acid rat model, Assay 4. In some illustrative embodiments, CNS-G001, while passing the HSP70 assay, did not exhibit sufficient activity under the test conditions to have warranted its being promoted to Assay 3, in which it showed that it had insufficient activity to have been of further interest, at 37% protection. Three compounds have been identified by the cascade of the first 3 assays that have protection >75% in the whole animal kainic acid model and will be considered for further study. Considering these compounds as representative, it is contemplated that the correlation between Assay 2 and the quantitative response of Assay 1b, is 78% and that Assay 3 is correlated 86% with Assay 2. From these results it can be reasonably concluded that the functional cascade proposed is adequate for the identification of compounds having superior performance to those that have already been identified.

The invention claimed is:

1. A method of treating amyotrophic lateral sclerosis (ALS), Alzheimer's disease (AD), or ischemia, the method comprising administering to a subject in need thereof a therapeutically effective amount of a compound selected from:

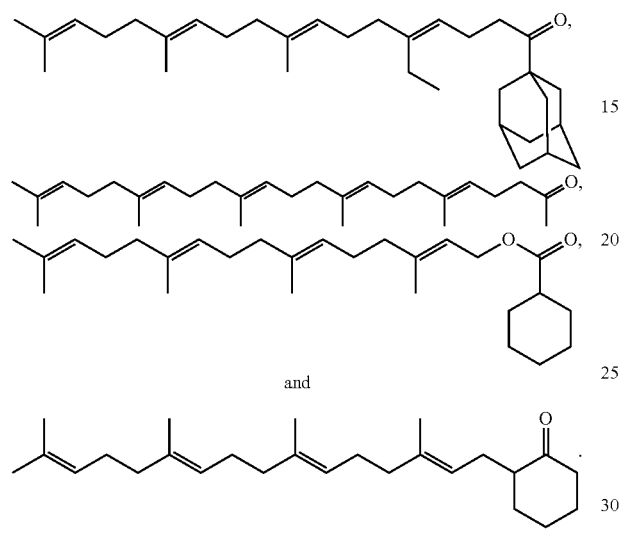

and